(12) United States Patent
Gao et al.

(10) Patent No.: US 10,883,148 B2
(45) Date of Patent: Jan. 5, 2021

(54) **MOLECULAR MARKERS ASSOCIATED WITH *OROBANCHE* RESISTANCE IN SUNFLOWER**

(71) Applicant: Dow AgroSciences LLC, Indianapolis, IN (US)

(72) Inventors: Wenxiang Gao, Rocklin, CA (US); Van L. Ripley, Grandora (CA); Chandra-Shekar A. Channabasavaradhya, West Sacramento, CA (US); David H. Meyer, Indianapolis, IN (US); Leonardo Velasco, Madrid (ES); Robert M. Benson, Ellsworth, WI (US); Begona Perez Vich, Madrid (ES); Angela L. Erickson, Fergus Falls, MN (US); Jose Maria Fernandez Martinez, Madrid (ES); Ruihua Ren, Carmel, IN (US); Milan Avery, Indianapolis, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 15/946,105

(22) Filed: Apr. 5, 2018

(65) Prior Publication Data

US 2019/0085413 A1    Mar. 21, 2019

Related U.S. Application Data

(60) Provisional application No. 62/482,368, filed on Apr. 6, 2017.

(51) Int. Cl.
| | | |
|---|---|---|
| *C12Q 1/68* | (2018.01) |
| *A01H 1/04* | (2006.01) |
| *C12Q 1/6895* | (2018.01) |
| *A01H 6/14* | (2018.01) |
| *G16B 30/00* | (2019.01) |
| *C12Q 1/6881* | (2018.01) |

(52) U.S. Cl.
CPC ............ *C12Q 1/6895* (2013.01); *A01H 1/04* (2013.01); *A01H 6/14* (2018.05); *A01H 6/1464* (2018.05); *C12Q 1/6881* (2013.01); *G16B 30/00* (2019.02); *C12Q 2600/13* (2013.01)

(58) Field of Classification Search
None
See application file for complete search history.

(56) References Cited

U.S. PATENT DOCUMENTS 7,872,170 B2 * 1/2011 Hassan ............... A01H 5/10
800/265

\* cited by examiner

*Primary Examiner* — Medina A Ibrahim

(57) ABSTRACT

This invention relates to methods for identifying sunflower plants that having increased *Orobanche* resistance. The methods use molecular markers to identify and to select plants with increased *Orobanche* resistance. Maize plants generated by the methods of the invention are also a feature of the invention.

8 Claims, 2 Drawing Sheets

Specification includes a Sequence Listing.

SEQUENCE LISTING

<160> NUMBER OF SEQ ID NOS: 32

<210> SEQ ID NO 1
<211> LENGTH: 120
<212> TYPE: DNA
<213> ORGANISM: Helianthus annuus
<220> FEATURE:
<221> NAME/KEY: misc_feature
<222> LOCATION: (58)..(58)
<223> OTHER INFORMATION: n = a, t, c or g

<400> SEQUENCE: 1
agtgattgtg ggagcatggt taggtgccgc tagatcgttg acaaacagt tcaccgcnct     60 raggcaagag gaggagctcg agaaggagat ggaaagagcc gcggttaaaa taccgattgt   120

<210> SEQ ID NO 2
<211> LENGTH: 41
<212> TYPE: DNA
<213> ORGANISM: Artificial Sequence
<220> FEATURE:
<223> OTHER INFORMATION: Chemically Synthesized

<400> SEQUENCE: 2
gaaggtgacc aagttcatgc tcgagctcct cctcttgcct t                        41

<210> SEQ ID NO 3
<211> LENGTH: 41
<212> TYPE: DNA
<213> ORGANISM: Artificial Sequence
<220> FEATURE:
<223> OTHER INFORMATION: Chemically Synthesized

```
<400> SEQUENCE: 3
gaaggtcgga gtcaacggat tcgagctcct cctcttgcct c                    41

<210> SEQ ID NO 4
<211> LENGTH: 25
<212> TYPE: DNA
<213> ORGANISM: Artificial Sequence
<220> FEATURE:
<223> OTHER INFORMATION: Chemically Synthesized

<400> SEQUENCE: 4
ccgctagatc gttggacaaa cagtt                                      25

<210> SEQ ID NO 5
<211> LENGTH: 120
<212> TYPE: DNA
<213> ORGANISM: Helianthus annuus
<220> FEATURE:
<221> NAME/KEY: misc_feature
<222> LOCATION: (65)..(65)
<223> OTHER INFORMATION: n = a, t, c or g

<400> SEQUENCE: 5
ttctaaaatc cacgtaaaag tacagtattt cgatgttaca caagatcgta actgggaccg    60
ygganttaaa agtgctaaat atcccggagt tccgtacacg ttctttggtc agagaaacgg   120

<210> SEQ ID NO 6
<211> LENGTH: 44
<212> TYPE: DNA
<213> ORGANISM: Artificial Sequence
<220> FEATURE:
<223> OTHER INFORMATION: Chemically Synthesized

<400> SEQUENCE: 6
gaaggtgacc aagttcatgc tcacaagatc gtaactggga ccgt                 44

<210> SEQ ID NO 7
<211> LENGTH: 43
<212> TYPE: DNA
<213> ORGANISM: Artificial Sequence
<220> FEATURE:
<223> OTHER INFORMATION: Chemically Synthesized

<400> SEQUENCE: 7
gaaggtcgga gtcaacggat tacaagatcg taactgggac cgc                  43

<210> SEQ ID NO 8
<211> LENGTH: 25
<212> TYPE: DNA
<213> ORGANISM: Artificial Sequence
<220> FEATURE:
<223> OTHER INFORMATION: Chemically Synthesized

<400> SEQUENCE: 8
cggaactccg ggatatttag cactt                                      25

<210> SEQ ID NO 9
<211> LENGTH: 99
<212> TYPE: DNA
<213> ORGANISM: Helianthus annuus
<220> FEATURE:
<221> NAME/KEY: misc_feature
<222> LOCATION: (97)..(97)
<223> OTHER INFORMATION: n = a, t, c or g

<400> SEQUENCE: 9
```

```
gagaaacgga tgtcgggttt cgttatatca agatgcgcac gtccccgatg gtttcattcc    60
yaaaataccc cttgctaacg gggaatttta cgagccnca                          99
```

<210> SEQ ID NO 10
<211> LENGTH: 45
<212> TYPE: DNA
<213> ORGANISM: Artificial Sequence
<220> FEATURE:
<223> OTHER INFORMATION: Chemically Synthesized

<400> SEQUENCE: 10

```
gaaggtgacc aagttcatgc ttccccgtta gcaaggggta tttta                   45
```

<210> SEQ ID NO 11
<211> LENGTH: 44
<212> TYPE: DNA
<213> ORGANISM: Artificial Sequence
<220> FEATURE:
<223> OTHER INFORMATION: Chemically Synthesized

<400> SEQUENCE: 11

```
gaaggtcgga gtcaacggat tccccgttag caagggggtat tttg                   44
```

<210> SEQ ID NO 12
<211> LENGTH: 22
<212> TYPE: DNA
<213> ORGANISM: Artificial Sequence
<220> FEATURE:
<223> OTHER INFORMATION: Chemically Synthesized

<400> SEQUENCE: 12

```
cgcacgtccc cgatggtttc at                                            22
```

<210> SEQ ID NO 13
<211> LENGTH: 119
<212> TYPE: DNA
<213> ORGANISM: Helianthus annuus
<220> FEATURE:
<221> NAME/KEY: misc_feature
<222> LOCATION: (99)..(99)
<223> OTHER INFORMATION: n = a, t, c or g

<400> SEQUENCE: 13

```
gatmccccgt ttcattcgct tttccgaacg cttgataccg cccaccatga cgatttccay    60
cagccgaact acaccggcgc ttccataacc aaaggcggnc ccgcgaacc gtggcacga     119
```

<210> SEQ ID NO 14
<211> LENGTH: 41
<212> TYPE: DNA
<213> ORGANISM: Artificial Sequence
<220> FEATURE:
<223> OTHER INFORMATION: Chemically Synthesized

<400> SEQUENCE: 14

```
gaaggtgacc aagttcatgc tcgccggtgt agttcggctg a                       41
```

<210> SEQ ID NO 15
<211> LENGTH: 40
<212> TYPE: DNA
<213> ORGANISM: Artificial Sequence
<220> FEATURE:
<223> OTHER INFORMATION: Chemically Synthesized

<400> SEQUENCE: 15
gaaggtcgga gtcaacggat tgccggtgta gttcggctgg        40

<210> SEQ ID NO 16
<211> LENGTH: 25
<212> TYPE: DNA
<213> ORGANISM: Artificial Sequence
<220> FEATURE:
<223> OTHER INFORMATION: Chemically Synthesized

<400> SEQUENCE: 16
ttgataccgc ccaccatgac gattt        25

<210> SEQ ID NO 17
<211> LENGTH: 251
<212> TYPE: DNA
<213> ORGANISM: Helianthus annuus

<400> SEQUENCE: 17
ttctgtcgga gttacctggg taattgttcg tttttgtatt cgattgttct accaaaaaga        60
aacatcatca tcatcggcat ccatagaacg tgatgtgttt aataggtata atgtggcraa       120
actctaacag ttgattcgtc caggttcgtt cgtggatgct tacatctctt tagattcgta       180
tgacgatcaa caaaacgcca ggattcgatt agtagctaag aagctgattg ttgattctaa       240
ctgaagggtt t        251

<210> SEQ ID NO 18
<211> LENGTH: 50
<212> TYPE: DNA
<213> ORGANISM: Artificial Sequence
<220> FEATURE:
<223> OTHER INFORMATION: Chemically Synthesized

<400> SEQUENCE: 18
gaaggtgacc aagttcatgc tgtgatgtgt ttaataggta taatgtggca        50

<210> SEQ ID NO 19
<211> LENGTH: 48
<212> TYPE: DNA
<213> ORGANISM: Artificial Sequence
<220> FEATURE:
<223> OTHER INFORMATION: Chemically Synthesized

<400> SEQUENCE: 19
gaaggtcgga gtcaacggat tgatgtgttt aataggtata atgtggcg        48

<210> SEQ ID NO 20
<211> LENGTH: 28
<212> TYPE: DNA
<213> ORGANISM: Artificial Sequence
<220> FEATURE:
<223> OTHER INFORMATION: Chemically Synthesized

<400> SEQUENCE: 20
aacctggacg aatcaactgt tagagttt        28

<210> SEQ ID NO 21
<211> LENGTH: 86
<212> TYPE: DNA
<213> ORGANISM: Helianthus annuus

<400> SEQUENCE: 21
tcaaaggatg tctttgacca gaaagcyagt aataagtact ggattgatgt ccagttgcgt        60
tggggtgatt atgattctca tgatat        86

```
<210> SEQ ID NO 22
<211> LENGTH: 47
<212> TYPE: DNA
<213> ORGANISM: Artificial Sequence
<220> FEATURE:
<223> OTHER INFORMATION: Chemically Synthesized

<400> SEQUENCE: 22
gaaggtgacc aagttcatgc tcaaaggatg tctttgacca gaaagct            47

<210> SEQ ID NO 23
<211> LENGTH: 46
<212> TYPE: DNA
<213> ORGANISM: Artificial Sequence
<220> FEATURE:
<223> OTHER INFORMATION: Chemically Synthesized

<400> SEQUENCE: 23
gaaggtcgga gtcaacggat taaaggatgt ctttgaccag aaagcc             46

<210> SEQ ID NO 24
<211> LENGTH: 29
<212> TYPE: DNA
<213> ORGANISM: Artificial Sequence
<220> FEATURE:
<223> OTHER INFORMATION: Chemically Synthesized

<400> SEQUENCE: 24
gcaactggac atcaatccag tacttatta                                29

<210> SEQ ID NO 25
<211> LENGTH: 120
<212> TYPE: DNA
<213> ORGANISM: Helianthus annuus
<220> FEATURE:
<221> NAME/KEY: misc_feature
<222> LOCATION: (94)..(95)
<223> OTHER INFORMATION: n = a, t, c or g

<400> SEQUENCE: 25
gggtcaaaag cgtcttggtc aacttgccaa gtggaaaaca gcagaagaag tggctgctct    60
kgttcgttcc ttacccgttg aagaacaacc caanncaaat cattgtgaca cgtaaaggaa   120

<210> SEQ ID NO 26
<211> LENGTH: 44
<212> TYPE: DNA
<213> ORGANISM: Artificial Sequence
<220> FEATURE:
<223> OTHER INFORMATION: Chemically Synthesized

<400> SEQUENCE: 26
gaaggtgacc aagttcatgc tcagcagaag aagtggctgc tctt               44

<210> SEQ ID NO 27
<211> LENGTH: 43
<212> TYPE: DNA
<213> ORGANISM: Artificial Sequence
<220> FEATURE:
<223> OTHER INFORMATION: Chemically Synthesized

<400> SEQUENCE: 27
gaaggtcgga gtcaacggat tagcagaaga agtggctgct ctg                43

<210> SEQ ID NO 28
```

```
<211> LENGTH: 25
<212> TYPE: DNA
<213> ORGANISM: Artificial Sequence
<220> FEATURE:
<223> OTHER INFORMATION: Chemically Synthesized

<400> SEQUENCE: 28
gggttgttct tcaacgggta aggaa                                         25

<210> SEQ ID NO 29
<211> LENGTH: 203
<212> TYPE: DNA
<213> ORGANISM: Helianthus annuus

<400> SEQUENCE: 29
ctgctgttgc ctccctgct actagtttct tgctgatcag gttcagtatg tgatgtatgt     60
caatctttta ttatgytgct gttgatctta aatatgatc tgtttggtat gtgtgttgat   120
tatgcgtata tagtcaaatt ttaacatggc ccgtttcgac ccgtacctat tattattatc   180
aaaagttcaa aacccatttt gac                                          203

<210> SEQ ID NO 30
<211> LENGTH: 52
<212> TYPE: DNA
<213> ORGANISM: Artificial Sequence
<220> FEATURE:
<223> OTHER INFORMATION: Chemically Synthesized

<400> SEQUENCE: 30
gaaggtgacc aagttcatgc tcaaacagat catattataa gatcaacagc aa           52

<210> SEQ ID NO 31
<211> LENGTH: 51
<212> TYPE: DNA
<213> ORGANISM: Artificial Sequence
<220> FEATURE:
<223> OTHER INFORMATION: Chemically Synthesized

<400> SEQUENCE: 31
gaaggtcgga gtcaacggat taaacagatc atattataag atcaacagca g            51

<210> SEQ ID NO 32
<211> LENGTH: 29
<212> TYPE: DNA
<213> ORGANISM: Artificial Sequence
<220> FEATURE:
<223> OTHER INFORMATION: Chemically Synthesized

<400> SEQUENCE: 32
gatcaggttc agtatgtgat gtatgtcaa                                     29
```

MOLECULAR MARKERS ASSOCIATED WITH *OROBANCHE* RESISTANCE IN SUNFLOWER

CROSS-REFERENCE TO RELATED APPLICATIONS

This application claims the benefit of U.S. Provisional application No. 62/482,368, filed Apr. 6, 2017, entitled "MOLECULAR MARKERS ASSOCIATED WITH OROBANCHE RESISTANCE IN SUNFLOWER", the disclosure of which is being incorporated by reference in its entirety.

REFERENCE TO SEQUENCE LISTING SUBMITTED ELECTRONICALLY

The official copy of the sequence listing is submitted electronically via EFS-Web as an ASCII formatted sequence listing with a file named "74816-US-PSP-20170406_ST25", created on Aug. 13, 2018, and having a size of 7.41 kilobytes, and is filed concurrently with the specification. The sequence listing contained in this ASCII formatted document is part of the specification, and is incorporated herein by reference in its entirety.

FIELD OF THE INVENTION

The present invention relates to methods useful in selecting for increased *Orobanche* resistance in sunflower plants.

BACKGROUND OF THE INVENTION

*Orobanche* (broomrape or broom-rape) is a genus of over 200 species of parasitic herbaceous plants in the family Orobanchaceae, mostly native to the temperate Northern Hemisphere. *Orobanche cumana* (sunflower broomrape) is an obligatory non-photosynthetic root parasitic plant of the sunflower (*Helianthus annuus* L.) plant. The broomrape plant is small, from 10-60 cm tall depending on species. It is best recognized by its yellow- to straw-colored stems completely lacking chlorophyll, bearing yellow, white, or blue snapdragon-like flowers. The flower shoots are scaly, with a dense terminal spike of between ten and twenty flowers in most species, although single in *O. uniflora*. The leaves are merely triangular scales. The seeds are minute, tan-to-brown, and blacken with age. These plants generally flower from late winter to late spring. When they are not flowering, no part of the plants is visible above the surface of the soil.

As they have no chlorophyll, they are totally dependent on other plants for nutrients. Broomrape seeds remain dormant in the soil, often for many years, until stimulated to germinate by certain compounds produced by living plant roots. Broomrape seedlings put out a root-like growth, which attaches to the roots of nearby hosts. Once attached to a host, the broomrape robs its host of water and nutrients.

What is the economic impact? This parasitic weed is a substantial threat in Europe, especially in countries around the Black Sea and in Spain. Molinero-Ruiz et al. 2013. In Russia, the impact of *O. cumana* is associated with the cultivation of *H. annuus* (sunflower) and is documented back to the early years of the twentieth century. More recently, the problem of *O. cumana* on sunflower has increased in Turkey. Bulgaria, Spain. Greece. Romania, Hungary. Israel and Serbia (Parker and Riches, 1993; ter Borg. 1994; Garcia-Torres et al., 1995). In all these countries serious losses have occurred on a cyclical basis as *O. cumana* has developed new virulence, overcoming any resistance that plant breeders have managed to introdxluce to the crop. Infected plants are smaller in head diameter, and susceptible varieties can expect to lose at least 50% of their yield and losses of 100% have been recorded. Levels of 4, 6, 8 and 25 *O. cumana* per host plant can lead to 20, 52. 82 and 90% losses, respectively (Shalom et al., 1988). Shindmva et al. (1998) recorded that affected sunflowers were shorter, with smaller head diameter and lower yield per head.

Genetic resistance to *O. cumana* is typically qualitative, or vertical, and therefore *O. cumana* populations are commonly classified into races. Vranceanu et alt, 1980. These races periodically surpass all available resistance sources. Eight races have been reported thus far. A-H, with races F, G and H being very commonly reported. Kaya, 2014. Genetic diversity, mutation, and selection within specific gene pools, and gene flow between wild and weedy *O. cumana* populations have been cited as possible reasons for the rapid emergence of new races of *O. cumana*. Pineda-Martos et al 2013. While the use of herbicides such as imidazolinone have some degree of efficacy and crop management solutions, including soil solarization can help with infestations, breeding for genetic resistance remains the most efficient method of controlling *Orobanche* infestation.

The present invention additionally provides methods for controlling weeds or undesired vegetation in the vicinity of a sunflower plant of the invention. One method comprises applying an effective amount of AHAS-inhibiting herbicide, particularly an imidazolinone or sulfonylurea herbicide, to the weeds and to the sunflower plant. Another method comprises contacting a sunflower seed of the present invention before sowing and/or after pregermination with an effective amount of an AHAS-inhibiting herbicide, particularly an imidazolinone or sulfonylurea herbicide. The present invention further provides the sunflower seeds of the present invention treated with an effective amount of an AHAS-inhibiting herbicide. The sunflower plants and seeds for use in these methods comprise in their genomes a first AHASL1 allele and a second AHASL1 allele. The first AHASL1 allele encodes a sunflower AHASL1 protein comprising the A122T amino acid substitution. The second AHASL1 allele encodes a sunflower AHASL1 protein comprising the A205V amino acid substitution or the P197L amino acid substitution.

The present invention further provides methods for controlling the parasitic weeds *Orobanche cumana* and *Orobanche cernua*, also known as broomrape, on infected sunflower plants. The method comprises applying an effective amount of an imidazolinone herbicide to the weeds and to the herbicide-resistant sunflower plant of the present invention, particularly a sunflower plant comprising two A122T alleles or a sunflower plant comprising one AHASL1 A122T allele and one A205V AHASL1 allele.

Breeding *Orobanche* resistance into sunflower is the principal and most effective control method to manage yield loss associated with *Orobanche* infestation. The development of molecular genetic markers has facilitated mapping and selection of agriculturally important traits in sunflowers, and quantitative trait loci (QTL) for *Orobanche* resistance have been identified. QTL conferring resistance to *Orobanche* resistance have been previously identified on LG4, 6, 9, 10, 11, 13, 15, 16 and 17. Louarn et al, 2016. However, because of the rapid rate at with *Orobanche* overcomes resistance, further sources of resistance are imperative.

Introgression of QTL through the use of molecular markers associated with *Orobanche* resistance will increase the speed and accuracy of moving *Orobanche* resistance into elite sunflower hybrids, thus improving the level of resistance in subtropical germplasm. Incorporating *Orobanche* resistance into elite sunflower germplasm may prevent the spread of the viral disease to non-endemic regions.

Despite the fact that information for *Orobanche* resistance QTL is available in the art, few pedigrees can be classified as highly tolerant and there is little evidence of any strong resistance to *Orobanche* resistance in commercially available hybrids. There is a need for commercially acceptable hybrids that are *Orobanche* resistance resistant and for a method to develop and track resistant sunflower inbreds and hybrids through marker assisted breeding.

Described within is a method to map *Orobanche* resistance QTL in a DH population using a bi-parental QTL mapping approach. The present invention allows selection of progeny which contain the genomic background of the agronomically desirable parent and the genomic trait of the *Orobanche* resistance resistant donor parent. The present invention also allows tracking of *Orobanche* resistance QTL in order to introgress the *Orobanche* resistance trait into new plants through traditional breeding.

SUMMARY OF THE INVENTION

One embodiment of the present invention is a method for selecting a plant having increased *Orobanche* resistance. The method includes the steps of: a) detecting at least one marker nucleic acid; and, b) selecting a plant comprising the marker nucleic acid, thereby selecting a plant having increased *Orobanche* resistance. The plant is preferably a sunflower plant.

In embodiments of the invention, the marker nucleic acid is selected from the group consisting of DHAI000240, DHAG000732, DHAI007796 and DHAI007334. In further embodiments of the invention, at least one marker nucleic acid is selected, and preferably, at least two marker nucleic acids are selected.

In another embodiment of the invention is a method for selecting a sunflower plant having increased *Orobanche* resistance, the method comprising: a) detecting at least one marker nucleic acids, wherein at least one marker nucleic acid is selected from the group consisting of DHAI000240, DHAG000732, DHAI007796 and DHAI007334; and, b) selecting a plant comprising at least one marker nucleic acids, thereby selecting a sunflower plant having increased *Orobanche* resistance. Sunflower plants obtained by the methods described herein are also contemplated by the present invention.

BRIEF DESCRIPTION OF FIGURES AND SEQUENCE LISTINGS

The invention can be more fully understood from the following detailed description and the accompanying drawings and Sequence Listing, which form a part of this application. The Sequence Listing contains the one letter code for nucleotide sequence characters and the three letter codes for amino acids as defined in conformity with the IUPAC-IUBMB standards described in Nucleic Acids Research 13:3021-3030 (1985) and in the Biochemical Journal 219 (No. 2): 345-373 (1984), which are herein incorporated by reference in their entirety. The symbols and format used for nucleotide and amino acid sequence data comply with the rules set forth in 37 C.F.R. § 1.822.

Figure 1:
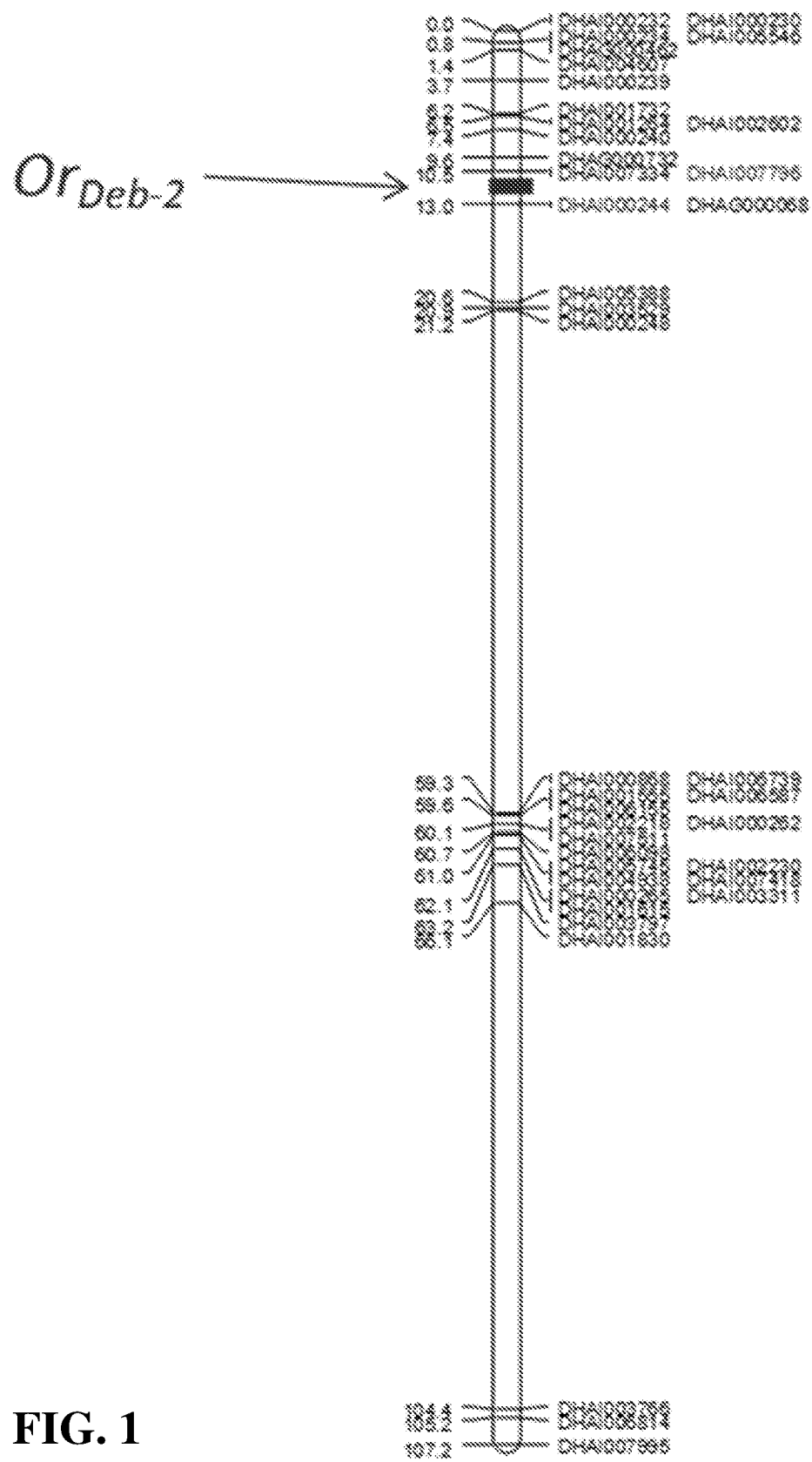
FIG. 1 shows the *Orobanche* resistant QTL Or$_{Deb-2}$ mapped to linkage group 4.

SEQ ID NO:1 is the sequence from which the DHAI000240 KASP™ assay was designed.

SEQ ID NO:2 is the allele 1 primer for the DHAI000240 KASP™ assay.

SEQ ID NO:3 is the allele 2 primer for the DHAI000240 KASP™ assay.

SEQ ID NO:4 is the common reverse primer for the DHAI000240 KASP™ assay.

SEQ ID NO:5 is the sequence from which the DHAI009612 KASP™ assay was designed.

SEQ ID NO:6 is the allele 1 primer for the DHAI009612 KASP™ assay.

SEQ ID NO:7 is the allele 2 primer for the DHAI009612 KASP™ assay.

SEQ ID NO:8 is the common reverse primer for the DHAI009612 KASP™ assay.

SEQ ID NO:9 is the sequence from which the DHAI000732 KASP™ assay was designed.

SEQ ID NO:10 is the allele 1 primer for the DHAG000732 KASP™ assay.

SEQ ID NO:11 is the allele 2 primer for the DHAG000732 KASP™ assay.

SEQ ID NO:12 is the common reverse primer for the DHAG000732 KASP™ assay.

SEQ ID NO:13 is the sequence from which the DHAI009613 KASP™ assay was designed.

SEQ ID NO:14 is the allele 1 primer for the DHAI009613 KASP™ assay.

SEQ ID NO:15 is the allele 2 primer for the DHAI009613 KASP™ assay.

SEQ ID NO:16 is the common reverse primer for the DHAI009613 KASP™ assay.

SEQ ID NO:17 is the sequence from which the DHAI007334 KASP™ assay was designed.

SEQ ID NO:18 is the allele 1 primer for the DHAI007334 KASP™ assay.

SEQ ID NO:19 is the allele 2 primer for the DHAI007334 KASP™ assay.

SEQ ID NO:20 is the common reverse primer for the DHAI007334 KASP™ assay.

SEQ ID NO:21 is the sequence from which the DHAI000243 KASP™ assay was designed.

SEQ ID NO:22 is the allele 1 primer for the DHAI000243 KASP™ assay.

SEQ ID NO:23 is the allele 2 primer for the DHAI000243 KASP™ assay.

SEQ ID NO:24 is the common reverse primer for the DHAI000243 KASP™ assay.

SEQ ID NO:25 is the sequence from which the DHAI009614 KASP™ assay was designed.

SEQ ID NO:26 is the allele 1 primer for the DHAI009614 KASP™ assay.

SEQ ID NO:27 is the allele 2 primer for the DHAI009614 KASP™ assay.

SEQ ID NO:28 is the common reverse primer for the DHAI009614 KASP™ assay.

SEQ ID NO:29 is the sequence from which the DHAI007796 KASP™ assay was designed.

SEQ ID NO:30 is the allele 1 primer for the DHAI007796 KASP™ assay.

SEQ ID NO:31 is the allele 2 primer for the DHAI007796 KASP™ assay.

SEQ ID NO:32 is the common reverse primer for the DHAI007796 KASP™ assay.

DETAILED DESCRIPTION OF THE INVENTION

The present invention provides methods for identifying and selecting sunflower plants with increased *Orobanche* resistance. The following definitions are provided as an aid to understand the invention.

The term "allele" refers to one of two or more different nucleotide sequences that occur at a specific locus.

An "amplicon" is amplified nucleic acid, e.g., a nucleic acid that is produced by amplifying a template nucleic acid by any available amplification method (e.g., PCR, LCR, transcription, or the like).

The term "amplifying" in the context of nucleic acid amplification is any process whereby additional copies of a selected nucleic acid for a transcribed form thereof are produced. Typical amplification methods include various polymerase based replication methods, including the polymerase chain reaction (PCR), ligase mediated methods such as the ligase chain reaction (LCR) and RNA polymerase based amplification (e.g., by transcription) methods.

The term "assemble" applies to bacterial artificial clones (BACs) and their propensities for coming together to form contiguous stretches of DNA. A BAC "assembles" to a contig based on sequence alignment, if the BAC is sequenced, or via the alignment of its BAC fingerprint to the fingerprints of other BACs.

An allele is "associated with" a trait when it is linked to it and when the presence of the allele is an indicator that the desired trait or trait form will occur in a plant comprising the allele.

A "bacterial artificial chromosome (BAC)" is a cloning vector derived from the naturally occurring F factor of *Escherichia coli*. BACs can accept large inserts of DNA sequence. In sunflower, a number of BACs, or bacterial artificial chromosomes, each containing a large insert of sunflower genomic DNA, have been assembled into contigs (overlapping contiguous genetic fragments, or "contiguous DNA").

"Backcrossing" refers to the process whereby hybrid progeny are repeatedly crossed back to one of the parents. In a backcrossing scheme, the "donor" parent refers to the parental plant with the desired gene or locus to be introgressed. The "recipient" parent (used one or more times) or "recurrent" parent (used two or more times) refers to the parental plant into which the gene or locus is being introgressed. For example, see Ragot, M. et al. (1995) Marker-assisted backcrossing: a practical example, in Techniques et Utilisations des Marqueurs Moleculaires Les Colloques, Vol. 72, pp. 45-56, and Openshaw et al., (1994) Marker-assisted Selection in Backcross Breeding, Analysis of Molecular Marker Data, pp. 41-43. The initial cross gives rise to the F1 generation: the term "BC1" then refers to the second use of the recurrent parent, "BC2" refers to the third use of the recurrent parent, and so on.

A centimorgan ("cM") is a unit of measure of recombination frequency. One cM is equal to a 1% chance that a marker at one genetic locus will be separated from a marker at a second locus due to crossing over in a single generation.

"Chromosomal interval" designates a contiguous linear span of genomic DNA that resides in plants on a single chromosome. The genetic elements or genes located on a single chromosomal interval are physically linked. The size of a chromosomal interval is not particularly limited. In some aspects, the genetic elements located within a single chromosomal interval are genetically linked, typically with a genetic recombination distance of, for example, less than or equal to 20 cM, or alternatively, less than or equal to 10 cM. That is, two genetic elements within a single chromosomal interval undergo recombination at a frequency of less than or equal to 20% or 10%, respectively.

The term "chromosomal interval" designates any and all intervals defined by any of the markers set forth in this invention. A chromosomal interval that correlates with increased *Orobanche* resistance is provided. This interval, located on LG4, comprises and is flanked by DHAI0000240 and DHAI007796. Three are at least three subintervals of chromosomal interval DHAI0000240 and DHAI007796: DHAI0000240 and DHAG000732, DHA000732 and DHAI007334, and DHAI007334 and DHAI007796.

The term "complement" refers to a nucleotide sequence that is complementary to a given nucleotide sequence, i.e., the sequences are related by the base-pairing rules.

The term "contiguous DNA" refers to overlapping contiguous genetic fragments.

The term "crossed" or "cross" means the fusion of gametes via pollination to produce progeny (e.g., cells, seeds or plants). The term encompasses both sexual crosses (the pollination of one plant by another) and selfing (self-pollination, e.g., when the pollen and ovule are from the same plant). The term "crossing" refers to the act of fusing gametes via pollination to produce progeny.

The term "elite line" refers to any line that has resulted from breeding and selection for superior agronomic performance. An elite plant is any plant from an elite line.

A "favorable allele" is the allele at a particular locus that confers, or contributes to, a desirable phenotype, e.g., increased *Orobanche* resistance, or alternatively, is an allele that allows the identification of plants with decreased *Orobanche* resistance that can be removed from a breeding program or planting ("counter-selection"). A favorable allele of a marker is a marker allele that segregates with the favorable phenotype, or alternatively, segregates with the unfavorable plant phenotype, therefore providing the benefit of identifying plants.

"Fragment" is intended to mean a portion of a nucleotide sequence. Fragments can be used as hybridization probes or PCR primers using methods disclosed herein.

A "genetic map" is a description of genetic linkage relationships among loci on one or more chromosomes (or chromosomes) within a given species, generally depicted in a diagrammatic or tabular form. For each genetic map, distances between loci are measured by the recombination frequencies between them, and recombinations between loci can be detected using a variety of molecular genetic markers (also called molecular markers). A genetic map is a product of the mapping population, types of markers used, and the polymorphic potential of each marker between different populations. The order and genetic distances between loci can differ from one genetic map to another. However, information such as marker position and order can be correlated between maps by determining the physical location of the markers on one of the sunflower linkage groups, Ha412HO bronze assembly reference genome, which is publicly available on the internet. One of ordinary skill in the art can use the publicly available genome browser to determine the physical location of markers on a chromosome.

The term "Genetic Marker" shall refer to any type of nucleic acid based marker, including but not limited to, Restriction Fragment Length Polymorphism (RFLP) (Botstein et al, 1998), Simple Sequence Repeat (SSR) (Jacob et al., 1991), Random Amplified Polymorphic DNA (RAPD) (Welsh et al., 1990), Cleaved Amplified Polymorphic Sequences (CAPS) (Rafalski and Tingey, 1993, Trends in Genetics 9:275-280), Amplified Fragment Length Polymorphism (AFLP) (Vos et al, 1995, Nucleic Acids Res. 23:4407-4414), Single Nucleotide Polymorphism (SNP) (Brookes, 1999, Gene 234:177-186), Sequence Characterized Amplified Region (SCAR) (Pecan and Michelmore, 1993, Theor. Appl. Genet, 85:985-993), Sequence Tagged Site (STS) (Onozaki et al. 2004, Euphytica 138:255-262), Single Stranded Conformation Polymorphism (SSCP) (Orita et al., 1989, Proc Natl Aced Sci USA 86:2766-2770). Inter-Simple Sequence Repeat (ISR) (Blair et al. 1999, Theor. Appl. Genet. 98:780-792), Inter-Retrotransposon Amplified Polymorphism (IRAP), Retrotransposon-Microsatellite Amplified Polymorphism (REMAP) (Kalendar et al., 1999, Theor. Appl. Genet 98:704-711), an RNA cleavage product (such as a Lynx tag), and the like.

"Genetic recombination frequency" is the frequency of a crossing over event (recombination) between two genetic loci. Recombination frequency can be observed by following the segregation of markers and/or traits following meiosis.

"Genome" refers to the total DNA, or the entire set of genes, carried by a chromosome or chromosome set.

The term "genotype" is the genetic constitution of an individual (or group of individuals) at one or more genetic loci, as contrasted with the observable trait (the phenotype). Genotype is defined by the allele(s) of one or more known loci that the individual has inherited from its parents. The term genotype can be used to refer to an individual's genetic constitution at a single locus, at multiple led, or, more generally, the term genotype can be used to refer to an individual's genetic make-up for all the genes in its genome.

"Germplasm" refers to genetic material of or from an individual (e.g., a plant), a group of individuals (e.g., a plant line, variety or family), or a clone derived from a line, variety, species, or culture. The germplasm can be part of an organism or cell, or can be separate from the organism or cell. In general, germplasm provides genetic material with a specific molecular makeup that provides a physical foundation for some or all of the hereditary qualities of an organism or cell culture. As used herein, germplasm includes cells, seed or tissues from which new plants may be grown, or plant parts, such as leafs, stems, pollen, or cells that can be cultured into a whole plant.

The "Ha415HO bronze assembly" sunflower reference genome is publicly available at the "Sunflower Genome Database". The "Sunflower Genome Database" also provides a number of other genomic resources, including high density genetic and physical maps, as well as transcriptome and sequence data for a diverse array of wild and cultivated genotypes.

A "haplotype" is the genotype of an individual at a plurality of genetic loci, i.e. a combination of alleles. Typically, the genetic loci described by a haplotype are physically and genetically linked, i.e., on the same chromosome segment. The term "haplotype" can refer to sequence, polymorphisms at a particular locus, such as a single marker locus, or sequence polymorphisms at multiple loci along a chromosomal segment in a given genome. The former can also be referred to as "marker haplotypes" or "marker alleles", while the latter can be referred to as "long-range haplotypes".

The "heritability ($h^2$)" of a trait within a population is the proportion of observable differences in a trait between individuals within a population that is due to genetic differences. The $h^2$ value of the QTL is a percentage of variation that is explained by genetics, instead of environment.

A "heterotic group" comprises a set of genotypes that perform well when crossed with genotypes from a different heterotic group (Hallauer at al. (1998) Corn breeding, p. 463-564. In G. F. Sprague and J. W. Dudley (ed) Corn and sunflower improvement). Inbred lines are classified into heterotic groups, and are further subdivided into families within a heterotic group, based on several criteria such as pedigree, molecular marker-based associations, and performance in hybrid combinations (Smith at al. (1990) Theor. Appl. Gen. 80:833-840).

The term "heterozygous" means a genetic condition wherein different alleles reside at corresponding loci on homologous chromosomes.

The term "homozygous" means a genetic condition wherein identical alleles reside at corresponding loci on homologous chromosomes.

"Hybridization" or "nucleic acid hybridization" refers to the pairing of complementary RNA and DNA strands as well as the pairing of complementary DNA single strands.

The term "hybridize" means the formation of base pairs between complementary regions of nucleic acid strands.

The term "indel" refers to an insertion or deletion, wherein one line may be referred to as having an insertion relative to a second line, or the second line may be referred to as having a deletion relative to the first line.

The term "introgression" or "introgressing" refers to the transmission of a desired allele of a genetic locus from one genetic background to another. For example, introgression of a desired allele at a specified locus can be transmitted to at least one progeny via a sexual cross between two parents of the same species, where at least one of the parents has the desired allele in its genome. Alternatively, for example, transmission of an allele can occur by recombination between two donor genomes, e.g., in a fused protoplast, where at least one of the donor protoplasts has the desired allele in its genome. The desired allele can be, e.g., a selected allele of a marker, a QTL, a transgene, or the like. In any case, offspring comprising the desired allele can be repeatedly backcrossed to a line having a desired genetic background and selected for the desired allele, to result in the allele becoming fixed in a selected genetic background. For example, the linkage group 4 locus described herein may be introgressed into a recurrent parent that is susceptible to *Orobanche* resistance. The recurrent parent line with the introgressed gene or locus then has increased *Orobanche* resistance.

As used herein, the term "linkage" is used to describe the degree with which one marker locus is associated with another marker locus or some other locus (for example, a *Orobanche* resistance locus). The linkage relationship between a molecular marker and a phenotype is given as a "probability" or "adjusted probability". Linkage can be expressed as a desired limit or range. For example, in some embodiments, any marker is linked (genetically and physically) to any other marker when the markers are separated by less than 50, 40, 30, 25, 20, or 15 map units for cM). In some aspects, it is advantageous to define a bracketed range of linkage, for example, between 10 and 20 cM, between 10 and 30 cM, or between 10 and 40 cM. The more closely a marker is linked to a second locus, the better an indicator for the second locus that marker becomes. Thus, "closely linked loci" such as a marker locus and a second locus display an inter-locus recombination frequency of 10% or less, preferably about 9% or less, still more preferably about 8% or less, yet more preferably about 7% or less, still more preferably about 6% or less, yet more preferably about 5% or less, still more preferably about 4% or less, yet more preferably about 3% or less, and still more preferably about 2% or less. In highly preferred embodiments, the relevant loci display a recombination frequency of about 1% or less, e.g., about 0.75% or less, more preferably about 0.5% or less, or yet more preferably about 0.25% or less. Two loci that are localized to the same chromosome, and at such a distance that recombination between the two loci occurs at a frequency of less than 10 (e.g., about 9%, 8%, 7%, 6%, 5%, 4%, 3%, 2%, 1%, 0.75%, 0.5%, 0.25%, or less) are also said to be "proximal to" each other. Since one cM is the distance between two markers that show a 1% recombination frequency, any marker is closely linked (genetically and physically) to any other marker that is in close proximity, e.g., at or less than 10 cM distant. Two closely linked markers on the same chromosome can be positioned 9, 8, 7, 6, 5, 4, 3, 2, 1, 0.75, 0.5 or 0.25 cM or less from each other.

The term "linkage disequilibrium" refers to a non-random segregation of genetic loci or traits for both loci. In either case, linkage disequilibrium implies that the relevant loci are within sufficient physical proximity along a length of a chromosome so that they segregate together with greater than random (i.e., non-random) frequency (in the case of co-segregating traits, the loci that underlie the traits are in sufficient proximity to each other). Markers that show linkage disequilibrium are considered linked. Linked loci co-segregate more than 50% of the time, e.g., from about 51% to about 100% of the time. In other words, two markers that co-segregate have a recombination frequency of less than 50% (and by definition, are separated by less than 50 cM on the same chromosome.) As used herein, linkage can be between two markers, or alternatively between a marker and a phenotype. A marker locus can be "associated with" (linked to) a trait, e.g., increased *Orobanche* resistance. The degree of linkage of a molecular marker to a phenotypic trait is measured, e.g. as a statistical probability of co-segregation of that molecular marker with the phenotype.

Linkage disequilibrium is most commonly assessed using the measure $r^2$, which is calculated using the formula described by Hill, W. G. and Robertson, A, Theor Appl. Genet 38:226-231 (1988). When $r^2=1$, complete LD exists between the two marker loci, meaning that the markers have not been separated by recombination and have the same allele frequency. Values for $r^2$ above ⅓ indicate sufficiently strong LD to be useful for mapping (Ardlie at al., Nature Reviews Genetics 3:299-309 (2002)). Hence, alleles are in linkage disequilibrium when $r^2$ values between pairwise marker loci are greater than or equal to 0.33, 0.4, 0.5, 0.6, 0.7, 0.8, 0.9, or 1.0.

As used herein, "linkage equilibrium" describes a situation where two markers independently segregate, i.e., sort among progeny randomly. Markers that show linkage equilibrium are considered unlinked (whether or not they lie on the same chromosome).

The "logarithm of odds (LOD) value" or "LOD score" (Risch, Science 255:803-804 (1992)) is used in interval mapping to describe the degree of linkage between two marker loci. A LOD score of three between two markers indicates that linkage is 1000 times more likely than no linkage, while a LOD score of two indicates that linkage is 100 times more likely than no linkage. LOD scores greater than or equal to two may be used to detect linkage.

A "locus" is a position on a chromosome where a gene or marker is located.

The term "sunflower plant" includes: whole sunflower plants, sunflower plant cells, sunflower plant protoplast, sunflower plant cell or sunflower tissue cultures from which sunflower plants can be regenerated, sunflower plant cells that are intact in sunflower plants or parts of sunflower plants, such as sunflower seeds, sunflower heads, sunflower flowers, sunflower cotyledons, sunflower leaves, sunflower stems, sunflower buds, sunflower roots, sunflower root tips, and the like.

"*Orobanche* (*Orobanche* spp)" are species of parasitic weeds which cause devastating crop losses for producers of Sunflowers.

A "marker" is a nucleotide sequence or encoded product thereof (e.g., a protein) used as a point of reference. For markers to be useful at detecting recombinations, they need to detect differences, or polymorphisms, within the population being monitored. For molecular markers, this means differences at the DNA level due to polynucleotide sequence differences (e.g. SSRs, RFLPs, AFLPs, SNPs). The genomic variability can be of any origin, for example, insertions, deletions, duplications, repetitive elements, point mutations, recombination events, or the presence and sequence of transposable elements. Molecular markers can be derived from genomic or expressed nucleic acids (e.g., ESTs) and can also refer to nucleic acids used as probes or primer pairs capable of amplifying sequence fragments via the use of PCR-based methods. A large number of sunflower molecular markers are known in the art, and are published or available from various sources.

Markers corresponding to genetic polymorphisms between members of a population can be detected by methods well-established in the art. These include, e.g., DNA sequencing, PCR-based sequence specific amplification methods, detection of RFLPs, detection of isozyme markers, detection of polynucleotide polymorphisms by allele specific hybridization (ASH), detection of amplified variable sequences of the plant genome, detection of self-sustained sequence replication, detection of SSRs, detection of SNPs, or detection of AFLPs. Well established methods are also known for the detection of expressed sequence tags (ESTs) and SSR markers derived from EST sequences and RAPDs.

A "marker allele", alternatively an "allele of a marker locus", can refer to one of a plurality of polymorphic nucleotide sequences found at a marker locus in a population that is polymorphic for the marker locus.

"Marker assisted selection" (MAS) is a process by which phenotypes are selected based on marker genotypes.

"Marker assisted counter-selection" is a process by which marker genotypes are used to identify plants that will not be selected, allowing them to be removed from a breeding program or planting.

A "marker locus" is a specific chromosome location in the genome of a species when a specific marker can be found. A marker locus can be used to track the presence of a second linked locus, e.g., a linked locus that encodes or contributes to expression of a phenotypic trait. For example, a marker locus can be used to monitor segregation of alleles at a locus, such as a QTL or single gene, that are genetically or physically linked to the marker locus.

A "marker probe" is a nucleic add sequence or molecule that can be used to identify the presence of a marker locus, e.g., a nucleic acid probe that is complementary to a marker locus sequence, through nucleic add hybridization. Marker probes comprising 30 or more contiguous nucleotides of the marker locus ("all or a portion" of the marker locus sequence) may be used for nucleic acid hybridization. Alternatively, in some aspects, a marker probe refers to a probe of any type that is able to distinguish (i.e. genotype) the particular allele that is present at a marker locus.

The term "molecular marker" may be used to refer to a genetic marker, as defined above, or an encoded product thereof (e.g., a protein) used as a point of reference when identifying a linked locus. A marker can be derived from genomic nucleotide sequences or from expressed nucleotide sequences (e.g., from a spliced RNA, a cDNA, etc.), or from an encoded polypeptide. The term also refers to nucleic acid sequences complementary to or flanking the marker sequences, such as nucleic acids used as probes or primer pairs capable of amplifying the marker sequence. A "molecular marker probe" is a nucleic acid sequence or molecule that can be used to identify the presence of a marker locus, e.g., a nucleic acid probe that is complementary to a marker locus sequence. Alternatively, in some aspects, a marker probe refers to a probe of any type that is able to distinguish (i.e., genotype) the particular allele that is present at a marker locus. Nucleic acids are "complementary" when they specifically hybridize in solution, e.g., according to Watson-Crick base pairing rules. Some of the markers described herein are also referred to as hybridization markers when located on an indel region, such as the non-collinear region described herein. This is because the insertion region is, by definition, a polymorphism vis a via a plant without the insertion. Thus, the marker need only indicate whether the indel region is present or absent. Any suitable marker detection technology may be used to identify such a hybridization marker, e.g., SNP technology is used in the examples provided herein.

"Nucleotide sequence", "polynucleotide", "nucleic acid sequence", and "nucleic acid fragment" are used interchangeably and refer to a polymer of RNA or DNA that is single- or double-stranded, optionally containing synthetic, non-natural or altered nucleotide bases. A "nucleotide" is a monomeric unit from which DNA or RNA polymers are constructed, and consists of a purine or pyrimidine base, a pentose, and a phosphoric acid group. Nucleotides (usually found in their 5'-monophosphate form) are referred to by their single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

The terms "phenotype", or "phenotypic trait" or "trait" refers to one or more traits of an organism. The phenotype can be observable to the naked eye, or by any other means of evaluation known in the art, e.g., microscopy, biochemical analysis, or an electromechanical assay. In some cases, a phenotype is directly controlled by a single gene or genetic locus, i.e., a "single gene trait". In other cases, a phenotype is the result of several genes.

A "physical map" of the genome is a map showing the linear order of identifiable landmarks (including genes, markers, etc.) on chromosome DNA. However, in contrast to genetic maps, the distances between landmarks are absolute (for example, measured in base pairs or isolated and overlapping contiguous genetic fragments) and not based on genetic recombination.

A "plant" can be a whole plant, any part thereof, or a cell or tissue culture derived from a plant. Thus, the term "plant" can refer to any of: whole plants, plant components or organs (e.g., leaves, stems, roots, etc.), plant tissues, seeds, plant cells, and/or progeny of the same. A plant cell is a cell of a plant, taken from a plant, or derived through culture from a cell taken from a plant.

A "polymorphism" is a variation in the DNA that is too common to be due merely to new mutation. A polymorphism must have a frequency of at least 1% in a population. A polymorphism can be a single nucleotide polymorphism, or SNP, or an insertion/deletion polymorphism, also referred to herein as an "indel".

The "probability value" or "p-value" is the statistical likelihood that the particular combination of a phenotype and the presence or absence of a particular marker allele is random. Thus, the lower the probability score, the greater the likelihood that a phenotype and a particular marker will co-segregate. In some aspects, the probability score is considered "significant" or "nonsignificant". In some embodiments, a probability score of 0.05 (p=0.05, or a 5% probability) of random assortment is considered a significant indication of co-segregation. However, an acceptable probability can be any probability of less than 50% (p=0.5). For example, a significant probability can be less than 0.25, less than 0.20, less than 0.15, less than 0.1, less than 0.05, less than 0.01, or less than 0.001.

The term "progeny" refers to the offspring generated from a cross.

A "progeny plant" is generated from a cross between two plants.

A "reference sequence" is a defined sequence used as a basis for sequence comparison. The reference sequence is obtained by genotyping a number of lines at the locus, aligning the nucleotide sequences in a sequence alignment program (e.g. Sequencher), and then obtaining the consensus sequence of the alignment.

A "single nucleotide polymorphism (SNP)" is an allelic single nucleotide-A, T, C or G-variation within a DNA sequence representing one locus of at least two individuals of the same species. For example, two sequenced DNA fragments representing the same locus from at least two individuals of the same species, AAGCCTA to AAGCTTA, contain a difference in a single nucleotide.

The phrase "under stringent conditions" refers to conditions under which a probe or polynucleotide will hybridize to a specific nucleic acid sequence, typically in a complex mixture of nucleic acids, but to essentially no other sequences. Stringent conditions are sequence-dependent and will be different in different circumstances.

Sequence alignments and percent identity calculations may be determined using a variety of comparison methods designed to detect homologous sequences including, but not limited to, the MEGALIGN® program of the LASERGENE® bioinformatics computing suite (DNASTAR® Inc., Madison, Wis.). Unless stated otherwise, multiple alignment of the sequences provided herein were performed using the Clustal V method of alignment (Higgins and Sharp, CABIOS. 5:151-153 (1989)) with the default parameters (GAP PENALTY=10, GAP LENGTH PENALTY=10), Default parameters for pairwise alignments and calculation of percent identity of protein sequences using the Clustal V method are KTUPLE=1, GAP PENALTY=3, WINDOW=5 and DIAGONALS SAVED=5. For nucleic adds these parameters are KTUPLE=2, GAP PENALTY=5, WINDOW=4 and DIAGONALS SAVED=4. After alignment of the sequences, using the Clustal V program, it is possible to obtain "percent identity" and "divergence" values by viewing the "sequence distances" table on the same program; unless stated otherwise, percent identities and divergences provided and claimed herein were calculated in this manner.

Before describing the present invention in detail, it should be understood that this invention is not limited to particular embodiments. It also should be understood that the terminology used herein is for the purpose of describing particular embodiments, and is not intended to be limiting. As used herein and in the appended claims, terms in the singular and the singular forms "a", "an" and "the", for example, include plural referents unless the content clearly dictates otherwise. Thus, for example, reference to "plant", "the plant" or "a plant" also includes a plurality of plants. Depending on the context, use of the term "plant" can also include genetically similar or identical progeny of that plant. The use of the term "a nucleic acid" optionally includes many copies of that nucleic acid molecule.

Genetic Mapping

It has been recognized for quite some time that specific genetic loci correlating with particular phenotypes, can be mapped in an organism's genome. The plant breeder can advantageously use molecular markers to identify desired individuals by detecting marker alleles that show a statistically significant probability of co-segregation with a desired phenotype, manifested as linkage disequilibrium. By identifying a molecular marker or clusters of molecular markers that co-segregate with a trait of interest, the breeder is able to rapidly select a desired phenotype by selecting for the proper molecular marker allele (a process called marker-assisted selection, or MAS).

A variety of methods well known in the art are available for detecting molecular markers or clusters of molecular markers that co-segregate with a trait of interest. The basic idea underlying these methods is the detection of markers, for which alternative genotypes (or alleles) have significantly different average phenotypes. Thus, one makes a comparison among marker loci of the magnitude of difference among alternative genotypes (or alleles) or the level of significance of that difference. Trait genes are inferred to be located nearest the marker(s) that have the greatest associated genotypic difference.

Two such methods used to detect trait loci of interest are: 1) Population-based association analysis and 2) Traditional linkage analysis. In a population-based association analysis, lines are obtained from pre-existing populations with multiple founders, e.g. elite breeding lines. Population-based association analyses rely on the decay of linkage disequilibrium (LD) and the idea that in an unstructured population, only correlations between genes controlling a trait of interest and markers closely linked to those genes will remain after so many generations of random mating. In reality, most pre-existing populations have population substructure. Thus, the use of a structured association approach helps to control population structure by allocating individuals to populations using data obtained from markers randomly distributed across the genome, thereby minimizing disequilibrium due to population structure within the individual populations (also called subpopulations). The phenotypic values are compared to the genotypes (alleles) at each, marker locus for each line in the subpopulation. A significant marker-trait association indicates the dose proximity between the marker locus and one or more genetic loci that are involved in the expression of that trait.

The same principles underlie traditional linkage analysis; however, LD is generated by creating a population from a small number of founders. The founders are selected to maximize the level of polymorphism within the constructed population, and polymorphic sites are assessed for their level of cosegregation with a given phenotype. A number of statistical methods have been used to identify significant marker-trait associations. One such method is an interval mapping approach (Lander and Botstein, Genetics 121:185-199 (1989), in which each of many positions along a genetic map (say at 1 cM intervals) is tested for the likelihood that a gene controlling a trait of interest is located at that position. The genotype/phenotype data are used to calculate for each test position a LOD score (log of likelihood ratio). When the LOD score exceeds a threshold value, there is significant evidence for the location of a gene controlling the trait of interest at that position on the genetic map (which will fall between two particular marker loci).

Markers Associated with *Orobanche* Resistance

Markers associated with increased *Orobanche* resistance are identified herein. The methods involve detecting the presence of at least one marker allele associated with the enhanced resistance in the germplasm of a sunflower plant. The marker locus can be selected from any of the marker loci provided in Table 1, including DHAI000240, DHAG000732, DHAI007796 and DHAI007334 and any other marker linked to these markers.

The genetic elements or genes located on a contiguous linear span of genomic DNA on a single chromosome are physically linked. DHAI000240, DHAG000732, DHAI007796 and DHAI007334, highly associated with *Orobanche* resistance, delineate an *Orobanche* resistance QTL. Any polynucleotide that assembles to the contiguous DNA between and including SEQ ID NO:1 (the reference sequence for DHAI0000240), or a nucleotide sequence that is 95% identical to SEQ ID NO:1 based on the Clustal V method of alignment, and SEQ ID NO:29 (the reference sequence for DHAI007796), or a nucleotide sequence that is 95% identical to SEQ ID NO:29 based on the Clustal V method of alignment, can house marker loci that are associated with *Orobanche* resistance.

The genetic elements or genes located on a contiguous linear span of genomic DNA on several linkage groups are physically linked for the subinterval of DHAI0000240 and DHAG000732. DHAI0000240 and DHAG000732, both highly associated with *Orobanche* resistance, delineate a *Orobanche* resistance QTL. Any polynucleotide that assembles to the contiguous DNA between and including SEQ ID NO:1 (the reference sequence for DHAI0000240), or a nucleotide sequence that is 95% identical to SEQ ID NO:1 based on the Clustal V method of alignment, and SEQ ID NO:9 (the reference sequence for DHAG000732), or a nucleotide sequence that 95% identical to SEQ ID NO:9 based on the Clustal V method of alignment, can house marker loci that are associated with *Orobanche* resistance.

The genetic elements or genes located on a contiguous linear span of genomic DNA on a single chromosome are physically linked for the subinterval of DHAG000732 and DHAI007334. DHAG000732 and DHAI007334, both highly associated with *Orobanche* resistance, delineate an *Orobanche* resistance QTL. Any polynucleotide that assembles to the contiguous DNA between and including SEQ ID NO:9 (the reference sequence for DHAG000732), or a nucleotide sequence that is 95% identical to SEQ ID NO:9 based on the Clustal V method of alignment, and SEQ ID NO: 17 (the reference sequence for DHAI007334), or a nucleotide sequence that 95% identical to SEQ ID NO:17 based on the Clustal V method of alignment, can house marker loci that are associated with *Orobanche* resistance.

The genetic elements or genes located on a contiguous linear span of genomic DNA on a single chromosome are physically linked for the subinterval of DHAI007334 and DHAI007796. DHAI007334 and DHAI007796, both highly associated with *Orobanche* resistance, delineate a

*Orobanche* resistance QTL. Any polynucleotide that assembles to the contiguous DNA between and including SEQ ID NO: 17 (the reference sequence for DHAI007334), or a nucleotide sequence that is 95% identical to SEQ ID NO:17 based on the Clustal V method of alignment, and SEQ ID NO:29 (the reference sequence for DHAI007796), or a nucleotide sequence that 95% identical to SEQ ID NO:29 based on the Clustal V method of alignment, can house marker loci that are associated with *Orobanche* resistance.

A common measure of linkage is the frequency with which traits cosegregate. This can be expressed as a percentage of cosegregation (recombination frequency) or in centiMorgans (cM). The cM is a unit of measure of genetic recombination frequency. One cM is equal to a 1% chance that a trait at one genetic locus will be separated from a trait at another locus due to crossing over in a single generation (meaning the traits segregate together 99% of the time). Because chromosomal distance is approximately proportional to the frequency of crossing over events between traits, there is an approximate physical distance that correlates with recombination frequency.

Marker loci are themselves traits and can be assessed according to standard linkage analysis by tracking the marker loci during segregation. Thus, one cM is equal to a 1% chance that a marker locus will be separated from another locus, due to crossing over in a single generation.

Other markers linked to the markers listed in Table 1 can be used to predict *Orobanche* resistance in a sunflower plant. This includes any marker within 50 cM of DHAI000240, DHAG000732, DHAI007796 and DHAI007334, the markers associated with *Orobanche* resistance. The closer a marker is to a gene controlling a trait of interest, the more effective and advantageous that marker is as an indicator for the desired trait. Closely linked loci display an inter-locus cross-over frequency of about 10% or less, preferably about 9% or less, still more preferably about 8% or less, yet more preferably about 7% or less, still more preferably about 6% or less, yet more preferably about 5% or less, still more preferably about 4% or less, yet more preferably about 3% or less, and still more preferably about 2% or less. In highly preferred embodiments, the relevant loci (e.g., a marker locus and a target locus) display a recombination frequency of about 1% or less, e.g., about 0.75% or less, more preferably about 0.5% or less, or yet more preferably about 0.25% or less. Thus, the loci are about 10 cM, 9 cM, 8 cM, 7 cM, 6 cM, 5 cM, 4 cM, 3 cM, 2 cM, 1 cM, 0.75 cM, 0.5 cM or 0.25 cM or less apart. Put another way, two loci that are localized to the same chromosome, and at such a distance that recombination between the two loci occurs at a frequency of less than 10% (e.g., about 9%, 8% 7%, 6%, 5%, 4%, 3%, 2% 1%, 0.75%, 0.5%, 0.25.degree., or less) are said to be "proximal to" each other.

Although particular marker alleles can show co-segregation with increased *Orobanche* resistance, it is important to note that the marker locus is not necessarily responsible for the expression of the *Orobanche* resistance phenotype. For example, it is not a requirement that the marker polynucleotide sequence be part of a gene that imparts increased *Orobanche* resistance (for example, be part of the gene open reading frame). The association between a specific marker allele and the increased *Orobanche* resistance phenotype is due to the original "coupling" linkage phase between the marker allele and the allele in the ancestral sunflower line from which the allele originated. Eventually, with repeated recombination, crossing over events between the marker and genetic locus can change this orientation. For this reason, the favorable marker allele may change depending on the linkage phase that exists within the resistant parent used to create segregating populations. This does not change the fact that the marker can be used to monitor segregation of the phenotype. It only changes which marker allele is considered favorable in a given segregating population.

The term "chromosomal interval" designates any and all intervals defined by any of the markers set forth in this invention. A chromosomal interval that correlates with *Orobanche* resistance is provided. This interval, located on Linkage Group 4, comprises and is flanked by DHAI0000240 and DHAI007796. Three are at least three subintervals of chromosomal interval DHAI0000240 and DHAI007796: DHAI0000240 and DHAG000732, DHA000732 and DHAI007334, and DHAI007334 and DHAI007796.

A variety of methods well known in the art are available for identifying chromosomal intervals. The boundaries of such chromosomal intervals are drawn to encompass markers that will be linked to the gene controlling the trait of interest. In other words, the chromosomal interval is drawn such that any marker that lies within that interval (including the terminal markers that define the boundaries of the interval) can be used as a marker for *Orobanche* resistance. The interval described above encompasses a cluster of markers that co-segregate with *Orobanche* resistance. The clustering of markers occurs in relatively small domains on the chromosomes, indicating the presence of a gene controlling the trait of interest in those chromosome regions.

The interval was drawn to encompass the markers that co-segregate with *Orobanche* resistance. The interval encompasses markers that map within the interval as well as the markers that define the termini. For example, DHAI0000240 and DHAI007796, separated by 3906661 bp based on the sequence of LG4 (from the Ha412HO bronze assembly found on the publicly available Sunflower Genome Database), define a chromosomal interval encompassing a cluster of markers that co-segregate with *Orobanche* resistance. A second example includes the subinterval, DHAI0000240 and DHAG000732, separated by 1522089 bp based on sequence of LG4, which defines a chromosomal interval encompassing a cluster of markers that co-segregate with *Orobanche* resistance. A third example includes the subinterval DHAG000732 and DHAI007334 separated by 1564876 bp based on the sequence of LG4 which defines a chromosomal interval encompassing a cluster of markers that co-segregate with *Orobanche* resistance. A fourth example includes the subinterval DHAI007334 and DHAI007796 separated by 819532 bp based on the sequence of LG4, which defines a chromosomal interval encompassing a cluster of markers that co-segregate with *Orobanche* resistance. An interval described by the terminal markers that define the endpoints of the interval will include the terminal markers and any marker localizing within that chromosomal domain, whether those markers are currently known or unknown.

Chromosomal intervals can also be defined by markers that are linked to (show linkage disequilibrium with) a marker of interest, and is a common measure of linkage disequilibrium (LD) in the context of association studies. If the $r^2$ value of LD between any LG4 marker locus lying within the interval of DHAI0000240 and DHAI007796, or one of the three subintervals of DHAI0000240 and DHAI007796: DHAI0000240 and DHAG000732, DHA000732 and DHAI007334, and DHAI007334 and DHAI007796, or any other subinterval of DHAI0000240 and DHAI007796, and an identified marker within that interval that has an allele associated with increased *Orobanche* resistance is greater than ⅓ (Ardlie et al. Nature Reviews Genetics 3:299-309 (2002)), the loci are linked.

A marker of the invention can also be a combination of alleles at marker loci, otherwise known as a haplotype. The skilled artisan would expect that there might be additional polymorphic sites at marker loci in and around the chromosome 2 markers identified herein, wherein one, or more polymorphic sites is in linkage disequilibrium (LD) with an allele associated with increased *Orobanche* resistance. Two particular alleles at different polymorphic sites are said to be in LD if the presence of the allele at one of the sites tends to predict the presence of the allele at the other site on the same chromosome (Stevens, Mol. Diag. 4:309-17 (1999)).

Marker Assisted Selection

Molecular markers can be used in a variety of, plant breeding applications (e.g. see Staub et al. (1996) Hortscience 729-741; Tanksley (1983) Plant Molecular Biology Reporter 1: 3-8). One of the main areas of interest is to increase the efficiency of backcrossing and introgressing genes using marker-assisted selection (MAS). A molecular marker that demonstrates linkage with a locus affecting a desired phenotypic trait provides a useful tool for the selection of the trait in a plant population. This is particularly true with traits that are difficult to phenotype due to their dependence on environmental conditions. This category includes traits related to the resistance to biotic and abiotic stresses. This category also includes traits that are very expensive to phenotype because of laborious artificial inoculation or maintenance of managed stress environments. Another category of traits includes those which are associated with destruction of plant per se. Destructive phenotyping has been a bottleneck to implement MAS for the seed quality traits. Because DNA marker assays are not environmentally dependent, are robust, reliable, less laborious, less costly and take up less physical space than field phenotyping, much larger populations can be assayed, increasing the chances of finding a recombinant with the target segment from the donor line moved to the recipient line. The closer the linkage, the more useful the marker, as recombination is less likely to occur between the marker and the gene causing the trait, which can result in false positives. Having flanking markers decreases the chances that false positive selection will occur as a double recombination event would be needed. The ideal situation is to have a marker in the gene itself, so that recombination cannot occur between the marker and the gene. Such a marker is called a 'perfect marker'.

When a gene is introgressed by MAS, it is not only the gene that is introduced but also the flanking regions (Gepts. (2002). Crop Sci; 42: 1780-1790). This is referred to as "linkage drag." In the case where the donor plant is highly unrelated to the recipient plant, these flanking regions carry additional genes that may code for agronomically undesirable traits. This "linkage drag" may also result in reduced yield or other negative agronomic characteristics even after multiple cycles of backcrossing into the elite sunflower line. This is also sometimes referred to as "yield drag." The size of the flanking region can be decreased by additional backcrossing, although this is not always successful, as breeders do not have control over the size of the region or the recombination breakpoints (Young et al. (1998) Genetics 120:579-585). In classical breeding it is usually only by chance that recombinations are selected that contribute to a reduction in the size of the donor segment (Tanksley et al. (1989). Biotechnology 7: 257-264).

Even after 20 backcrosses in backcrosses of this type, one may expect to find a sizeable piece of the donor chromosome still linked to the gene being selected. With markers however, it is possible to select those rare individuals that have experienced recombination near the gene of interest. In 150 backcross plants, there is a 95% chance that at least one plant will have experienced a crossover within 1 cM of the gene, based on a single meiosis map distance. Markers will avow unequivocal identification of those individuals. With one additional backcross of 300 plants, there would be a 95% chance of a crossover within 1 cM single meiosis map distance of the other side of the gene, generating a segment around the target gene of less than 2 cM based on a single meiosis map distance. This can be accomplished in two generations with markers, while it would have required on average 100 generations without markers (See Tanksley et al., supra). When the exact location of a gene is known, flanking markers surrounding the gene can be utilized to select for recombinations in different population sizes. For example, in smaller population sizes, recombinations may be expected further away from the gene, so more distal flanking markers would be required to detect the recombination.

The key components to the implementation of MAS are (i) Defining the population within which the marker-trait association will be determined, which can be a segregating population, or a random or structured population; (ii) monitoring the segregation or association of polymorphic markers relative to the trait, and determining linkage or association using statistical methods; (iii) defining a set of desirable markers based on the results of the statistical analysis, and (iv) the use and/or extrapolation of this information to the current set of breeding germplasm to enable marker-based selection decisions to be made. The markers described in this disclosure, as well as other marker types such as SSRs and FLPs, can be used in marker assisted selection protocols.

SSRs can be defined as relatively short runs of tandemly repeated DNA with lengths of 6 bp or less (Tautz (1989) Nucleic Acid Research 17: 6463-6471; Wang et al. (1994) Theoretical and Applied Genetics, 88:1-6). Polymorphisms arise due to variation in the number of repeat units, probably caused by slippage during DNA replication (Levinson and Gutman (1987) Mol Biol Evol 4: 203-221). The variation in repeat length may be detected by designing PCR primers to the conserved non-repetitive flanking regions (Weber and May (1989) Am J Hum Genet. 44:388-396), SSRs are highly suited to mapping and MAS as they are multi-allelic, codominant, reproducible and amenable to high throughput automation (Rafalski et al. (1996) Generating and using DNA markers in plants. In Non-mammalian genomic analysis: a practical guide. Academic Press, pp 75-135).

Various types of SSR markers can be generated, and SSR profiles from resistant lines can be obtained by gel electrophoresis of the amplification products. Scoring of marker genotype is based on the size of the amplified fragment.

Various types of FLP markers can also be generated. Most commonly, amplification primers are used to generate fragment length polymorphisms. Such FLP markers are in many ways similar to SSR markers, except that the region amplified by the primers is not typically a highly repetitive region. Still, the amplified region, or amplicon, will have sufficient variability among germplasm, often due to insertions or deletions, such that the fragments generated by the amplification primers can be distinguished among polymorphic individuals.

SNP markers detect single base pair nucleotide substitutions. Of all the molecular marker types, SNPs are the most abundant, thus having the potential to provide the highest genetic map resolution (Bhattramakki et al. 2002 Plant Molecular Biology 48:539-547). SNPs can be assayed at an even higher level of throughput than SSRs, in a so-called 'ultra-high-throughput' fashion, as they do not require large amounts of DNA and automation of the assay may be straight-forward. SNPs also have the promise of being relatively low-cost systems. These three factors together make SNPs highly attractive for use in MAS. Several methods are available for SNP genotyping, including but not limited to, hybridization, primer extension, oligonucleotide ligation, nuclease cleavage, minisequencing and coded spheres. Such methods have been reviewed in: Gut (2001) Hum Mutat 17 pp, 475-492: Shi (2001) Clin Chem 47, pp. 164-172; Kwok (2000) Pharmacogenomics 1, pp. 95-100: Bhattramakki and Rafalski (2001) Discovery and application of single nucleotide polymorphism markers in plants. In: R, J Henry, Ed, Plant Genotyping: The DNA Fingerprinting of Plants, CABI Publishing, VVallingford. A wide range of commercially available technologies utilize these and other methods to interrogate SNPs including Masscode™. (Qiagen), Invader® (Third Wave Technologies), SnapShot® (Applied Biosystems), Taqman® (Applied Biosystems) and Beadarrays™ (Illumina).

A number of SNPs together within a sequence, or across linked sequences, can be used to describe a haplotype for any particular genotype (Ching et al. (2002), BMC Genet. 3:19 pp Gupta et al. 2001, Rafalski (2002b), Plant Science 162:329-333). Haplotypes can be more informative than, single SNPs and can be more descriptive of any particular genotype. For example, single SNP may be allele 'T' for a specific line or variety with increased *Orobanche* resistance, but the allele 'T' might also occur in the sunflower breeding population being utilized for recurrent parents. In this case, a haplotype, e.g. a combination of alleles at linked SNP markers, may be more informative. Once a unique haplotype has been assigned to a donor chromosomal region, that haplotype can be used in that population or any subset thereof to determine whether an individual has a particular gene. See, for example, WO2003054229. Using automated high throughput marker detection platforms known to those of ordinary skill in the art makes this process highly efficient and effective.

The sequences listed in Table 1 can be readily used to obtain additional polymorphic SNPs (and other markers) within the QTL interval listed in this disclosure. Markers within the described map region can be hybridized to BACs or other genomic libraries, or electronically aligned with genome sequences, to find new sequences in the same approximate location as the described markers.

In addition to SSRs, FLPs and SNPs, as described above, other types of molecular markers are also widely used, including but not limited to, markers derived from EST sequences, RAPDs, and other nucleic acid based markers.

Isozyme profiles and linked morphological characteristics can, in some cases, also be indirectly used as markers. Even though they do not directly detect DNA differences, they are often influenced by specific genetic differences. However, markers that detect DNA variation are far more numerous and polymorphic than isozyme or morphological markers (Tanksley (1983) Plant Molecular Biology Reporter 1:3-8).

Sequence alignments or contigs may also be used to find sequences upstream or downstream of the specific markers listed herein. These new sequences, close to the markers described herein, are then used to discover and develop functionally equivalent markers. For example, different physical and/or genetic maps are aligned to locate equivalent markers not described within this disclosure but that are within similar regions. These maps may be within the sunflower species, or even across other species whose genomes share some level of colinearity at macro- and micro-level with sunflower, such as rice and sorghum.

In general, MAS uses polymorphic markers that have been identified as having a significant likelihood of co-segregation with *Orobanche* resistance. Such markers are presumed to map near quantitative trait loci (QTL), give the plant its *Orobanche* resistance resistant phenotype, and are considered indicators, or markers, for the desired trait. Markers test sunflower plants for the presence of a desired allele, and those which contain a desired genotype at one or more loci are expected to transfer the desired genotype, along with a desired phenotype, to their progeny. The means to identify sunflower plants that have increased *Orobanche* resistance by identifying plants that have a specified allele at any one of marker loci described herein, including DHAI000240, DHAG000732, DHAI007796 and DHAI007334 are presented herein.

The interval presented herein finds use in MAS to select plants that demonstrate increased *Orobanche* resistance. Any marker that maps within the LG4 interval defined by and including DHAI000240 and DHAI007796 can be used for this purpose. In addition, haplotypes comprising alleles at one or more marker loci within LG4 intervals defined by and including DHAI000240 and DHAG000732, DHAG000732 and DHAI007334, or DHAI007334 and DHAI007796 can be used to introduce increased *Orobanche* resistance into sunflower lines or varieties. Any allele or haplotype that is in linkage disequilibrium with an allele associated with increased *Orobanche* resistance can be used in MAS to select plants with increased *Orobanche* resistance.

EXAMPLES

The following examples are offered to illustrate, but not to limit, the appended claims. It is understood that the examples and embodiments described herein are for illustrative purposes only and that persons skilled in the art will recognize various reagents or parameters that can be altered without departing from the spirit of the invention or the scope of the appended claims.

Example 1: Mapping Population and Phenotypic Data

An $F_2$ mapping population for *Orobanche* resistance was generated from the cross between a susceptible DAS proprietary B-line and a resistant line, Deb-2, obtained from Consejo Superior de Investigaciones Cientfficas (CSIC). Deb-2 carries resistant gene(s) to *Orobanche* race G from *Helianthus debilis*. The mapping population consisted of 289 $F_2$ individuals in addition to the parents.

The population was screened for *Orobanche* resistance to race G. The sunflower seeds were germinated in pots in the absence of *Orobanche*. Two days after germination, the germinated seeds were planted in soil infected with *Orobanche*, race G. Irrigation of plants was stopped after the $38^{th}$ day and the evaluation process began. At 45 days, the soil and plants were removed from the pot and plants were scored based on emergence of Orobanche plants into the categories of "resistant (no emergence of Orobanche plants)" or "susceptible (1 or more Orobanche plants). Five plants for each $F_2$ were scored.

Example 2: Genotyping the $F_2$ Population and QTL Mapping

Figure 2:
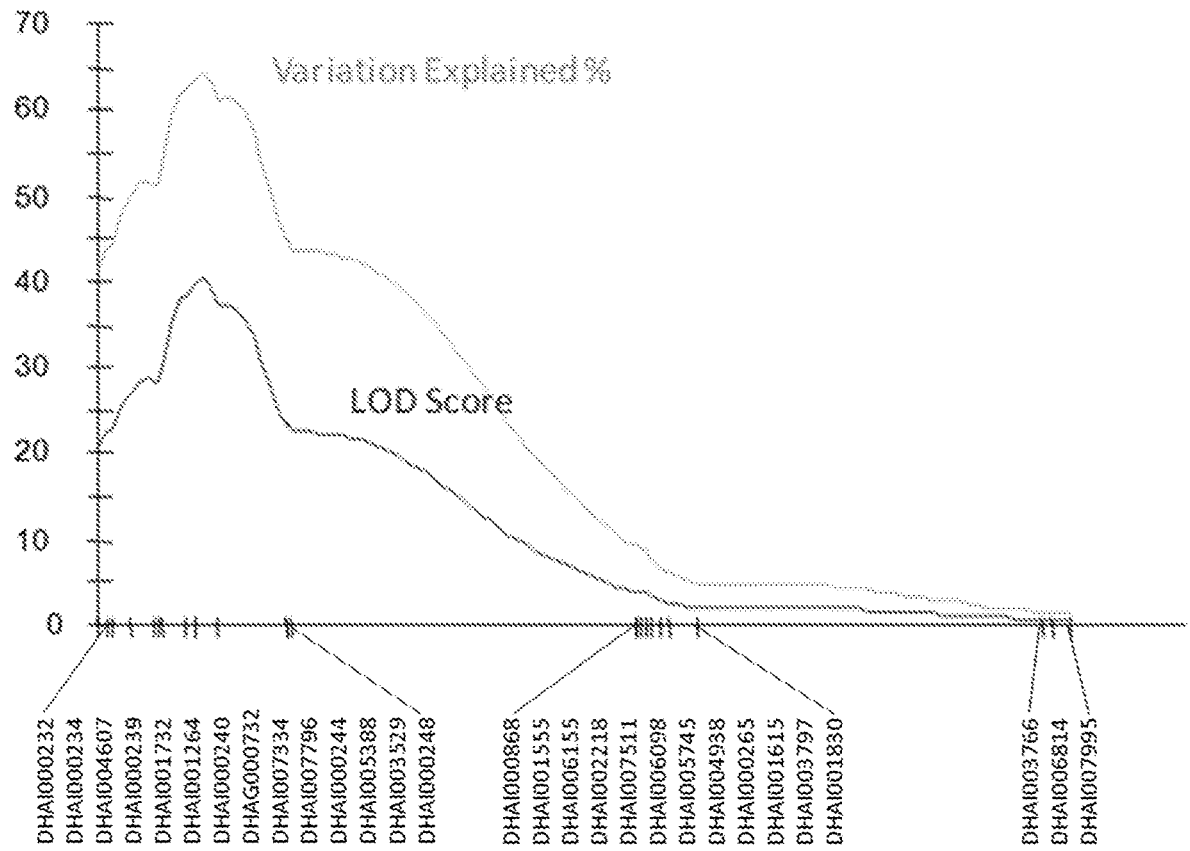
FIG. 2 shows the peak LOD score and percent variation explained for the QTL on linkage group 4.

One hundred and eight individuals from the $F_2$ population were genotyped with a DAS proprietary 9,000-SNP sunflower Infinium chip (Illumina, San Diego, Calif.). A genomic linkage map, comprised of 807 SNP markers across 20 linkage groups, was generated. A major resistant QTL, $Or_{Deb-2}$, was mapped to sunflower genome linkage group 4 (LG 4; FIG. 1). The QTL explained 64.4% of the total phenotypic variation in the $F_2$ mapping population and had a LOD score 40.4 (FIG. 2). The QTL peak occurred in the 3906780 bp interval between SNP markers DHAI000240 and DHAI007796.

JoinMap 4.0 (Van Ooijen, J W et al, 2006) was used to create the genetic linkage map. JoinMap 4.0 required only one input file from the population, referred to as a locus genotype file. In the locus genotype file of DH population, susceptible parent alleles were called "A", resistant parent alleles were called "B". Missing data were represented with a dash (-) in the locus genotype file. MapQTL 6.0 (Van Ooijen, J W et al, 2008) was used to map the QTLs. MapQTL 6.0 required three input files, including a locus genotype file, a map file, and a quantitative data file. The locus genotype file (loc file) contained the genotype codes for all loci of the segregating population as described above. The map file was generated from JoinMap and contained the estimated map positions of all loci. The quantitative data file (qua file) contained the Orobanche scores for each line of the mapping population. Interval mapping method was performed. When a LOD score exceeded the significance threshold (1000 permutation test results) on a linkage group, a segregating QTL was detected; the position with the largest LOD on the linkage group was the estimated position of the QTL on the map.

Markers identified in the QTL interval using MapQTL 6.0 were blasted against the publicly available sunflower reference genome, Ha412HO bronze assembly, to determine the physical locations of the markers. Physical locations of the markers are described in Table 1.

Example 3: Competitive Allele Specific PCR (KASPar™) Assay Design

The KASPar™ assays were designed with the Kraken™ workflow manager (LGC Genomics, Beverly, Mass.) using the assay design sequences which were the genomic sequences flanking the SNPs. The markers in the QTL interval, related sequences, and resistant alleles are described in Table 1.

SNP genotyping was performed using KASP™ SNP assays. A volume of 2 µl of DNA (1.5-2.5 ng/µl) was dispensed into 384 well PCR plates. The plates were centrifuged for 1 minute at 3000 rpm and dried for 2 hours at 65° C. The KASP™ reaction mix was prepared using 1×KASP™ Master Mix (LGC Genomics, Beverly, Mass.) as described by the manufacturer and 4.0 µl of reaction mix was added to the PCR plates. Plates were laser-sealed with an optically clear permanent seal and were centrifuged for 5 minutes at 3000 rpm. Thermal cycling was completed using the touchdown PCR program in the Hydrocycler™ (LGC Genomics) with the following conditions: 94° C. for 15 minutes followed by 10 cycles of 94° C. for 20 seconds and touchdown over 65-57° C. for 60 seconds (dropping 0.8° C. per cycle). This was followed by 29 cycles at 94° C. for 20 seconds and 57° C. annealing for 60 seconds. Following PCR, the plates were centrifuged at 2500 rpm for 1 minute and the resulting products were analyzed using the PHERAStar microplate reader (BMG Labtech, Cary, N.C.) employing FAM and HEX dye chemistries to distinguish between genotypes. The data was subsequently scored using the KlusterCaller application within the Kraken Laboratory Information Management System (LGC Genomics).

Following the completion of the KASP™ PCR and fluorescence reading, the raw fluorescence intensity data directly from the plate reader were analyzed in the Kraken Workflow Manager™ (LGC Genomics). A graph with RFU (relative fluorescence unit) of FAM as x-axis and VIC or HEX as y-axis was generated. Determinations of zygosity were made based on the cluster separation in a cluster view.

TABLE 1

KASP ™ assay sequences for the SNP markers located in the LG 4 QTL interval for $Or_{Deb-2}$. Physical position of markers are based on the Ha412HO bronze assembly.

| Marker_Name | Assay Design Seq (SEQ ID NO:) | Primer_A1 (SEQ ID NO:) | Primer_A2 (SEQ ID NO:) | Primer_Common (SEQ ID NO:) | SNP | Resistant Allele | Physical Position start (bp) | Physical Position end (bp) |
|---|---|---|---|---|---|---|---|---|
| DHAI000240 | 1 | 2 | 3 | 4 | A/G | A:A | 10391258 | 10391139 |
| DHAI009612 | 5 | 6 | 7 | 8 | T/C | T:T | 11913150 | 11913269 |
| DHAG000732 | 9 | 10 | 11 | 12 | T/C | C:C | 11913261 | 11913356 |
| DHAI009613 | 13 | 14 | 15 | 16 | T/C | C:C | 11913832 | 11913950 |
| DHAI007334 | 17 | 18 | 19 | 20 | A/G | G:G | 13478387 | 13478137 |
| DHAI000243 | 21 | 22 | 23 | 24 | T/C | T:T | 14151908 | 14151823 |
| DHAI009614 | 25 | 26 | 27 | 28 | T/G | T:T | 14150262 | 14150144 |
| DHAI007796 | 29 | 30 | 31 | 32 | T/C | C:C | 14297717 | 14297919 |

Example 4: Validation of Markers

Markers associated with the Orobanche QTL on LG 4 were screened against a second population with a Deb-2 source of resistance crossed with a susceptible elite line. The parents and 180 progeny were phenotyped as previously described and then genotyped with DHAI000240, DHAG000732, DHAI007796 and DHAI007334. The 128 progeny with resistant phenotypes also had resistant or heterozygous genotypes. The 52 progeny with susceptible phenotypes also had a susceptible genotypes (Table 2).

TABLE 2

Results of marker validation on second population with Deb-2 resistance.

| Germplasm | Pheno. | No. Shoots | DHAI000240 | DHAG000732 | DHAI007334 | DHAI007796 |
|---|---|---|---|---|---|---|
| Suscept. Elite | S | — | A | A | A | A |
| Deb-2 Donor | R | — | B | B | B | B |
| D2-2 | R | 0 | B | B | B | B |
| D2-3 | R | 0 | H | H | H | H |
| D2-4 | R | 0 | B | B | B | B |
| D2-5 | R | 0 | B | B | B | B |
| D2-6 | R | 0 | H | H | H | H |
| D2-7 | R | 0 | B | B | B | B |
| D2-8 | R | 0 | B | B | B | B |
| D2-9 | R | 0 | H | H | H | H |
| D2-10 | R | 0 | H | H | H | H |
| D2-14 | R | 0 | H | H | H | H |
| D2-15 | R | 0 | H | H | H | H |
| D2-16 | S | 16 | A | A | A | A |
| D2-17 | R | 0 | B | B | B | B |
| D2-18 | R | 0 | B | B | B | B |
| D2-19 | R | 0 | H | H | H | H |
| D2-20 | R | 0 | H | H | H | H |
| D2-21 | S | 15 | A | A | A | A |
| D2-22 | R | 0 | H | H | H | H |
| D2-23 | S | 20 | A | A | A | — |
| D2-24 | R | 0 | H | H | H | H |
| D2-25 | R | 0 | B | B | B | B |
| D2-27 | R | 0 | H | H | H | H |
| D2-28 | R | 0 | H | H | H | H |
| D2-29 | S | 22 | A | A | A | A |
| D2-30 | S | 17 | A | A | A | — |
| D2-33 | R | 0 | B | B | B | B |
| D2-34 | R | 0 | H | H | H | H |
| D2-36 | R | 0 | H | H | H | H |
| D2-37 | S | 5 | A | A | A | A |
| D2-38 | R | 0 | B | B | B | B |
| D2-40 | R | 0 | H | H | H | H |
| D2-41 | S | 18 | H | A | A | A |
| D2-42 | S | 11 | A | A | A | A |
| D2-46 | S | 5 | A | A | A | A |
| D2-47 | R | 0 | H | H | H | H |
| D2-50 | R | 0 | H | B | B | B |
| D2-51 | S | 9 | A | A | A | A |
| D2-52 | R | 0 | H | B | B | B |
| D2-53 | R | 0 | H | H | H | H |
| D2-54 | S | 22 | A | A | A | A |
| D2-55 | S | 9 | A | A | A | A |
| D2-56 | S | 10 | A | A | A | — |
| D2-57 | S | 8 | A | A | A | — |
| D2-59 | R | 0 | H | H | H | H |
| D2-60 | R | 0 | B | B | B | B |
| D2-61 | S | 32 | A | A | A | A |
| D2-62 | S | 6 | A | A | A | A |
| D2-63 | R | 0 | H | H | H | H |
| D2-64 | S | 20 | A | A | A | — |
| D2-65 | R | 0 | H | H | H | H |
| D2-66 | R | 0 | H | H | H | H |
| D2-67 | S | 6 | A | A | A | — |
| D2-68 | S | 11 | A | A | A | A |
| D2-70 | R | 0 | H | H | H | H |
| D2-71 | S | 5 | A | A | A | A |
| D2-72 | R | 0 | B | B | B | B |
| D2-73 | S | 8 | A | A | A | A |
| D2-74 | R | 0 | H | H | H | H |
| D2-75 | R | 0 | B | B | B | B |
| D2-76 | R | 0 | H | H | H | H |
| D2-77 | R | 0 | H | H | H | H |
| D2-78 | R | 0 | B | B | B | B |
| D2-79 | R | 0 | B | B | B | B |
| D2-80 | R | 0 | H | H | H | H |
| D2-81 | R | 0 | B | B | B | B |
| D2-82 | R | 0 | B | B | B | B |
| D2-83 | S | 25 | A | A | A | A |
| D2-84 | R | 0 | H | H | H | H |
| D2-85 | R | 0 | H | H | H | H |
| D2-86 | R | 0 | B | B | B | B |
| D2-87 | R | 0 | H | H | H | H |
| D2-88 | R | 0 | H | H | B | B |
| D2-89 | R | 0 | H | H | H | H |
| D2-90 | S | 9 | A | A | A | A |

TABLE 2-continued

Results of marker validation on second population with Deb-2 resistance.

| Germplasm | Pheno. | No. Shoots | DHAI000240 | DHAG000732 | DHAI007334 | DHAI007796 |
|---|---|---|---|---|---|---|
| D2-91 | S | 10 | A | A | A | A |
| D2-92 | R | 0 | B | B | B | B |
| D2-93 | R | 0 | B | B | B | B |
| D2-94 | R | 0 | B | B | B | B |
| D2-95 | R | 0 | B | B | B | B |
| D2-96 | R | 0 | H | H | H | H |
| D2-97 | R | 0 | A | H | H | H |
| D2-98 | R | 0 | B | B | B | B |
| D2-99 | R | 0 | H | H | H | H |
| D2-100 | R | 0 | H | H | H | H |
| D2-101 | S | 11 | A | A | A | — |
| D2-102 | S | 11 | H | A | A | — |
| D2-103 | R | 0 | H | H | H | H |
| D2-104 | R | 0 | H | B | B | B |
| D2-106 | R | 0 | A | H | H | H |
| D2-107 | R | 0 | H | H | H | H |
| D2-108 | R | 0 | H | H | H | H |
| D2-109 | S | 6 | A | A | A | A |
| D2-111 | R | 0 | H | H | H | H |
| D2-112 | S | 8 | A | A | A | A |
| D2-113 | R | 0 | B | B | B | B |
| D2-116 | S | 6 | A | A | A | A |
| D2-117 | R | 0 | H | H | H | H |
| D2-118 | S | 3 | A | A | A | A |
| D2-123 | R | 0 | H | H | H | H |
| D2-124 | R | 0 | H | H | H | H |
| D2-125 | R | 0 | H | H | H | H |
| D2-130 | S | 16 | A | A | A | A |
| D2-131 | R | 0 | H | H | H | H |
| D2-132 | R | 0 | H | H | H | H |
| D2-133 | R | 0 | H | H | H | H |
| D2-134 | R | 0 | H | H | H | H |
| D2-135 | R | 0 | H | H | H | H |
| D2-136 | R | 0 | B | B | B | B |
| D2-137 | R | 0 | H | H | H | H |
| D2-138 | R | 0 | H | H | H | H |
| D2-140 | S | 10 | A | A | A | — |
| D2-141 | R | 0 | H | H | H | H |
| D2-142 | R | 0 | B | B | B | B |
| D2-144 | S | 4 | A | A | A | — |
| D2-146 | S | 5 | A | A | A | A |
| D2-147 | R | 0 | H | H | H | H |
| D2-148 | S | 7 | H | H | A | A |
| D2-149 | R | 0 | H | H | H | H |
| D2-150 | S | 50 | A | A | A | A |
| D2-152 | S | 17 | A | A | A | A |
| D2-153 | S | 6 | A | A | A | — |
| D2-155 | R | 0 | H | H | H | H |
| D2-156 | R | 0 | B | B | B | B |
| D2-157 | R | 0 | H | H | H | — |
| D2-158 | R | 0 | H | H | H | H |
| D2-159 | R | 0 | H | H | H | H |
| D2-161 | R | 0 | B | B | B | B |
| D2-162 | S | 22 | A | A | A | A |
| D2-163 | R | 0 | B | B | B | B |
| D2-166 | R | 0 | B | B | B | B |
| D2-167 | R | 0 | H | H | H | H |
| D2-168 | R | 0 | H | H | H | H |
| D2-170 | S | 15 | A | A | A | A |
| D2-171 | S | 17 | A | A | A | A |
| D2-172 | S | 12 | H | H | A | — |
| D2-173 | R | 0 | H | H | H | — |
| D2-175 | R | 0 | H | H | H | H |
| D2-176 | R | 0 | B | B | B | B |
| D2-177 | S | 20 | A | A | A | A |
| D2-178 | R | 0 | H | H | H | H |
| D2-180 | R | 0 | H | H | H | H |
| D2-181 | R | 0 | B | B | B | B |
| D2-182 | R | 0 | H | H | H | H |
| D2-183 | S | 12 | A | A | A | A |
| D2-184 | R | 0 | H | H | H | H |
| D2-185 | R | 0 | B | B | B | B |
| D2-186 | R | 0 | H | H | H | H |
| D2-187 | R | 0 | H | H | H | H |
| D2-188 | R | 0 | B | B | B | B |
| D2-189 | R | 0 | B | B | B | B |

TABLE 2-continued

Results of marker validation on second population with Deb-2 resistance.

| Germplasm | Pheno. | No. Shoots | DHAI000240 | DHAG000732 | DHAI007334 | DHAI007796 |
|---|---|---|---|---|---|---|
| D2-191 | R | 0 | B | B | B | B |
| D2-192 | R | 0 | B | B | B | B |
| D2-193 | R | 0 | H | H | H | H |
| D2-194 | R | 0 | H | H | H | H |
| D2-195 | S | 7 | A | A | A | — |
| D2-196 | R | 0 | H | H | H | H |
| D2-197 | R | 0 | H | H | H | H |
| D2-198 | R | 0 | H | H | H | H |
| D2-199 | R | 0 | H | H | H | H |
| D2-201 | R | 0 | B | B | B | B |
| D2-202 | R | 0 | H | H | H | H |
| D2-203 | R | 0 | A | H | H | H |
| D2-204 | R | 0 | H | H | H | H |
| D2-205 | R | 0 | B | B | B | B |
| D2-206 | R | 0 | H | H | H | H |
| D2-207 | S | 17 | A | A | A | A |
| D2-208 | S | 9 | A | A | A | A |
| D2-209 | R | 0 | B | B | B | B |
| D2-210 | S | 22 | A | A | A | A |
| D2-211 | R | 0 | H | H | H | H |
| D2-212 | S | 16 | A | A | A | A |
| D2-213 | R | 0 | H | H | H | H |
| D2-214 | S | 37 | A | A | A | A |
| D2-215 | R | 0 | H | H | H | H |
| D2-216 | R | 0 | H | H | H | H |
| D2-217 | R | 0 | B | B | B | B |
| D2-218 | S | 16 | A | A | A | A |
| D2-219 | S | 29 | A | A | A | A |
| D2-220 | R | 0 | H | H | H | H |
| D2-221 | R | 0 | H | H | H | H |

Number of Orobanche shoots, phenotypic and genotypic calls are provided, where S = susceptible, R = resistant, A = susceptible allele, B = resistant allele, and H = heterozygous.

---

We claim:

1. A method for obtaining a sunflower plant that displays increased Orobanche resistance, the method comprising the steps of: a) detecting at least one marker nucleic acid selected from the group consisting of DHAI000240, DHAG000732, DHAI007796 and DHAI007334; b) selecting a first sunflower plant comprising the marker nucleic acid, thereby selecting a sunflower plant that displays increased Orobanche resistance, and c) crossing the first sunflower plant with a second sunflower plant to obtain said sunflower plant that displays increased Orobanche resistance.

2. The method of claim 1, wherein at least two marker nucleic acids are detected.

3. The method of claim 1, wherein at least three marker nucleic acids are detected.

4. The method of claim 1, wherein at least four marker nucleic acids are detected.

5. A method for introducing the increased Orobanche resistance into a sunflower plant, the method comprising: a) crossing a sunflower plant having increased Orobanche resistance with a second sunflower plant to generate F1 sunflower plants; b) detecting in the F1 sunflower plants at least one marker nucleic acid, wherein the at least one marker nucleic acid is selected from the group consisting of DHAI000240, DHAG000732, DHA1007796 and DHA1007334; and, c) selecting a plant comprising the at least one marker nucleic acids, thereby introducing increased Orobanche resistance into the sunflower plant.

6. A method of obtaining an Orobanche resistant sunflower plant comprising a quantitative trait locus ("QTL") associated with Orobanche resistance, the method comprising: (i) detecting at least one nucleic acid from the sunflower, which nucleic acid localizes to a linkage group interval flanked on each side by one or more marker pairs selected from among: a) DHAI0000240 and DHA1007796; b) DHAI0000240 and DHAG000732; c) DHA000732 and DHAI007334, and d) DHAI007334 and DHAI007796; (ii) selecting a first sunflower plant comprising the nucleic acid, thereby identifying the Orobanche resistant sunflower plant that displays increased Orobanche resistance; and, (iii) crossing the first sunflower plant with a second sunflower plant to obtain said sunflower plant that displays increased Orobanche resistance.

7. The method of claim 1, wherein the Orobanche resistance is Orobanche race G resistance from *Helianthus debilis*.

8. The method of claim 5, wherein the Orobanche resistance is Orobanche race G resistance from *Helianthus debilis*.

\* \* \* \* \*